United States Patent [19]

Strother

[11] Patent Number: 5,186,513
[45] Date of Patent: Feb. 16, 1993

[54] SOFTSHELL

[76] Inventor: Sander Strother, 3909 Navajo, Bakersfield, Calif. 93309

[21] Appl. No.: 843,727

[22] Filed: Feb. 28, 1992

[51] Int. Cl.⁵ .............................................. B62D 25/06
[52] U.S. Cl. .................... 296/100; 296/104; 296/105; 135/88
[58] Field of Search ....................... 296/100, 104, 105; 135/88

[56] References Cited

U.S. PATENT DOCUMENTS

| 2,565,746 | 8/1951 | Turner | 296/104 |
| 2,955,874 | 10/1960 | Brindley | 296/104 |
| 4,285,539 | 8/1981 | Cole | 296/105 |
| 4,639,034 | 1/1987 | Amos | 296/100 |
| 4,738,274 | 4/1988 | Heath | 296/100 |
| 4,756,325 | 7/1988 | Daniels | 296/105 |
| 4,813,734 | 3/1989 | Hoover | 296/100 |
| 4,883,305 | 11/1989 | Horton | 296/105 |
| 4,915,440 | 4/1990 | Daniel et al. | 296/104 |

*Primary Examiner*—Robert R. Song

[57] ABSTRACT

This cargo bay cover is a convenient, water-resistant, soft cover for a cargo bay. The cover is designed with five easily removable support arms (38) covered with a lightweight, water-resistant material (20). The support arms are steadied by rigid support brackets (32,34) which fit tightly around the upper side-wall ridge (82) of the cargo bay. Tension caused by the design of the support arms (38) pressing against the support brackets (32,34), and the stabilizer members (36), steady the cover during use. When the cover is not needed it can be removed, rolled up (FIG. 7), and stored in a handy storage bag (80).

18 Claims, 4 Drawing Sheets

SOFTSHELL

BACKGROUND

1. Field of Invention

The invention relates primarily to pick-up cargo bay covers, particularly flexible covers of a temporary nature.

2. Description of Prior Art

There are a large number of cargo covers for pick-up cargo bays in the prior art. Most of the prior art is designed to be a permanent addition to the cargo bay. An example is U.S. Pat. No. 4,915,440 issued Apr. 10, 1990 to A. Daniel et al in which U-shaped support arms are supported by brackets that are permanently installed to the interior side-wall of the pick-up truck. Further this invention requires that snap fasteners be permanently installed on the outside of the side-wall to secure the cover. While this cover can be removed from the cargo bay, the permanent support brackets and snap fasteners cannot be removed. Also this patent, as well as the other patents described in this section, cannot be easily disassembled to enable the art to be stored in a reasonably small storage bag.

U.S. Pat. No. 4,883,305 issued Nov. 28, 1989 to P. Horton, U.S. Pat. No. 4,756,325 issued Jul. 12, 1988 to D. Daniels, U.S. Pat. No. 4,639,034 issued Jan. 27, 1987 to J. Amos, and U.S. Pat. No. 4,285,539 issued Aug. 25, 1981 to R. Cole all require a permanent track system be installed on the cargo bay so the cover can be retracted when not in use. While these track system inventions do uncover the cargo bay when not in use, it does limit the usefulness of the front of the cargo bay nearest the cab. In all four of these inventions the cover is permanently stored at the front end of the cargo bay when not in use.

OBJECTS AND ADVANTAGES

Accordingly, several objects and advantages of my cover are:

(a) To provide a cargo bay cover that does not require any permanent attachments to the cargo bay.

(b) To provide a cargo bay cover that can be completely removed from the cargo bay.

(c) To provide a cargo bay cover that can be broken down and stored in a convenient storage bag.

Further objects and advantages are to provide a cargo bay cover with simplified construction and ease of use so that it can be easily handled by one lay person. While there is a great deal of art in the area of truck bed covers, this invention claims a substantial improvement by describing a cover that while sturdy, is completely removable and portable. Still further objects and advantages will become apparent from the consideration of the ensuing description and drawings.

DRAWINGS FIGURES

REFERENCE NUMERALS IN DRAWINGS

Figure 1:
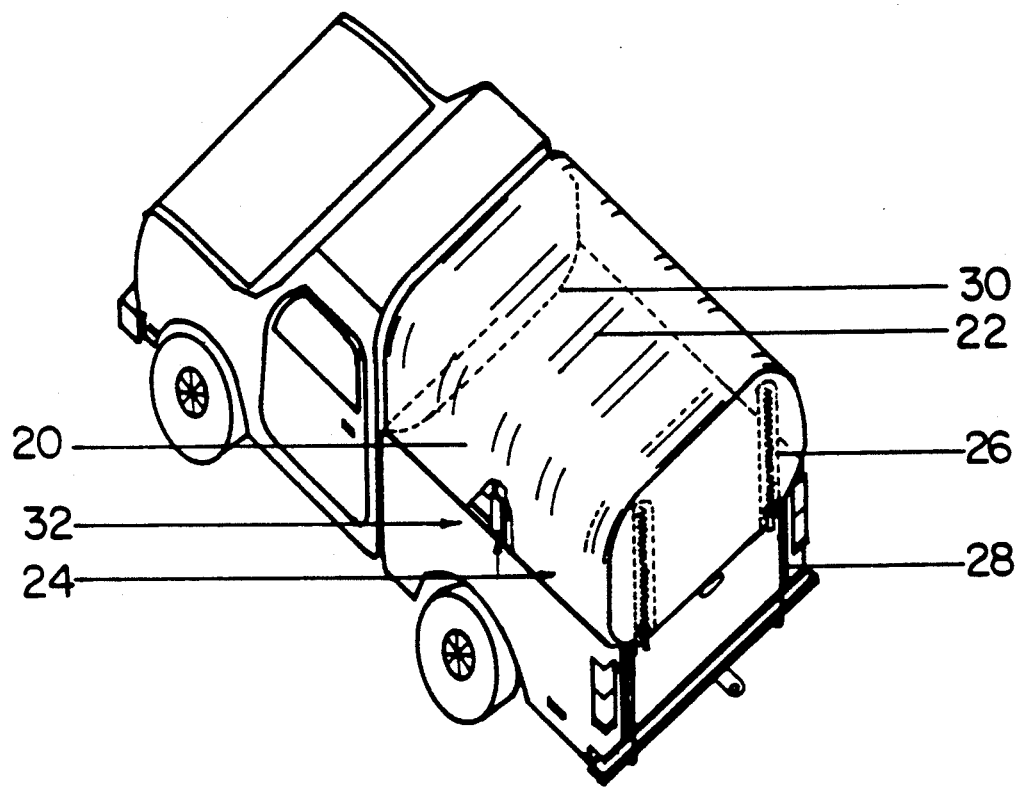
FIG. 1 shows a typical pick-up truck with the cover attached.
Figure 2:
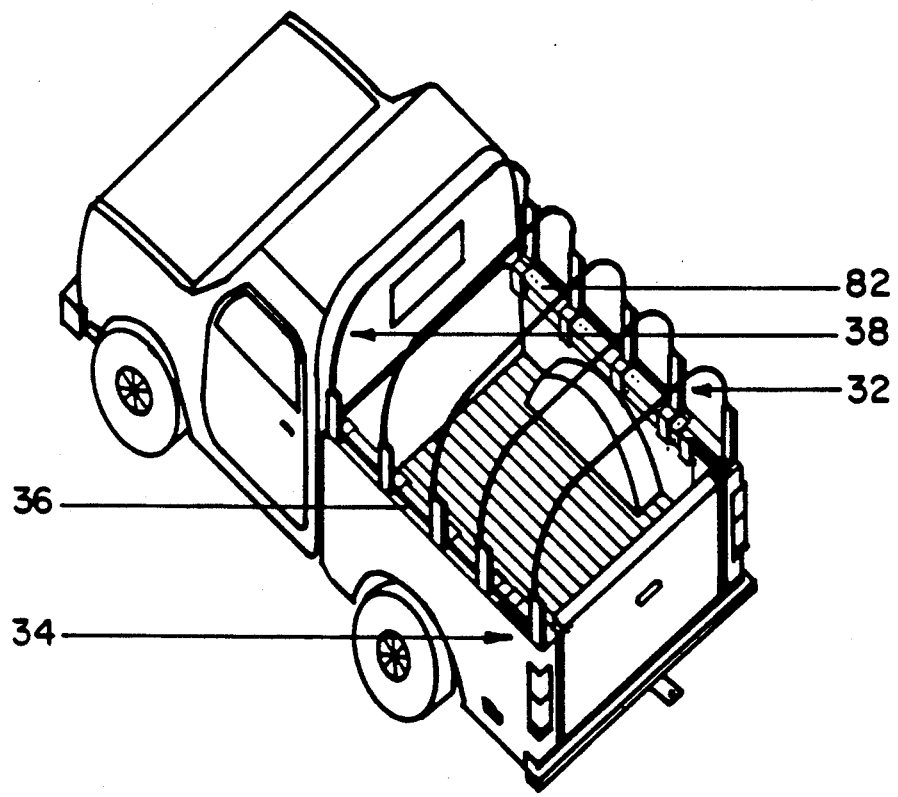
FIG. 2 shows the frame construction of the cover.
Figure 3:
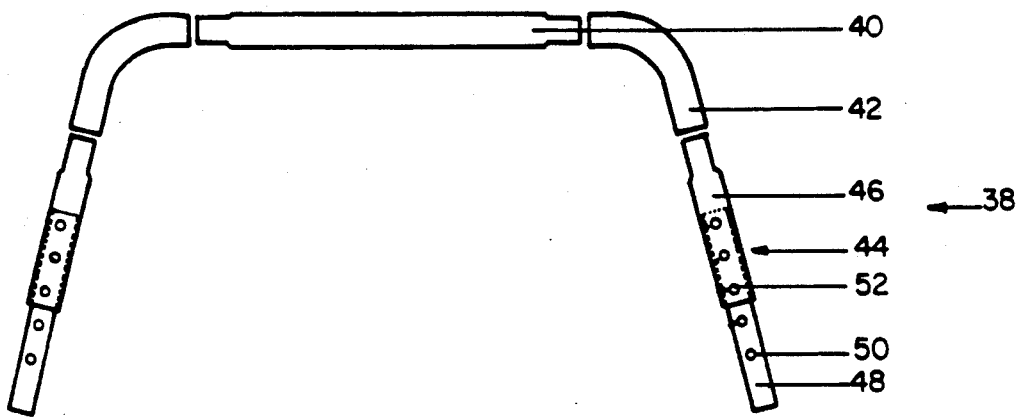
FIG. 3 shows the construction of a support arm.

| | |
|---|---|
| 20 flexible cover | 22 fabric support arm sleeves |
| 24 industrial snaps | 26 zipper |
| 28 elastic cord | 30 front cover flap |
| 32 sidewall support bracket | 34 tailgate support bracket |
| 36 stabilizer member | 38 support arm |
| 40 horizontal support arm | 42 elbow |
| 44 vertical support arm | 46 female support arm tube |
| 48 male support arm tube | 50 bolt receiving hole |
| 52 bolt | 54 machine bent metal bracket |
| 56 securing tube | 58 receiving tube |
| 60 extended securing tube | 62 machine bent "C" bracket |
| 64 receiving tube support | 66 bracket extensions |
| 66A upper bracket extension | 66B lower bracket extension |
| 68 male tube | 70 female tube |
| 72 cover storage | 74 assorted support brackets |
| 76 assorted elbows | 78 assorted tubing |
| 80 storage bag | 82 side-wall ridge |

DESCRIPTION—FIGS. 1 TO 8

It is to be understood the embodiment of this invention is not limited to the type of materials or construction format presented below. This disclosure represents the concept and basic construction of the convenient removable cargo bay cover. It is the purpose of this invention to provide a new and improved cargo bay cover with all of the advantages of the previous art with none of the disadvantages.

Referring to figure number one the flexible cover (20) is made of a lightweight, water-resistant material. The support arms (38, shown in figure two) slip through fabric sleeves (22) sewn into the underside of the cover. The fabric sleeves are used to properly position and support the support arms (38, shown in figure two). Zippers (26) above the tailgate allow easy access into the cargo bay without having to remove the cover. The cover itself is designed to slightly drape over the bottom of the tailgate. The cover is secured by elastic cords (28) that are sewn into the cover and hooked to the bottom of the bumper. The front of the cover (30) is designed to drape between the cargo bay and the cab to repel water and minimize the effect of the wind to the front of the cover. The cover is further held into place with the use of industrial snaps (24) attached to the main frame of the invention.

Figure number two shows the main frame of the invention. The invention is attached to the side-wall ridge (82) by the side-wall support brackets (32) and the tailgate support brackets (34). Both brackets (32,34) wrap around the side-wall ridge (82) to form a tight fit. Five support arms (38) are attached to the brackets (32,34) by bracket receiving tubes (58, shown in figure 4) to form the basic frame. A stabilizer member (36) is attached to the support brackets (32,34) by the securing tubes (56, shown in FIG. 4) to stabilize the frame.

Figure three shows a detail of a support arm (38). There are five of these support arms (all exactly the same) used in the main frame. A lower male tube (48) is attached to an upper female tube (46) by a bolt (52). Each tube (46,48) has evenly spaced holes (50) that can be used to adjust the height of a vertical support arm (44). A vertical support arm (44) slides into an elbow (42). A support arm extension (40) slides into the other end of the elbow (42). The other side of the support arm (38) is similarly constructed. Elbows (42) are designed to be at obtuse angles so that when support arms (38) are attached to the support brackets (32,34) they will exert pressure against the support brackets (32,34) which will in turn exert pressure against the side-wall ridge (82).

Figure 4:
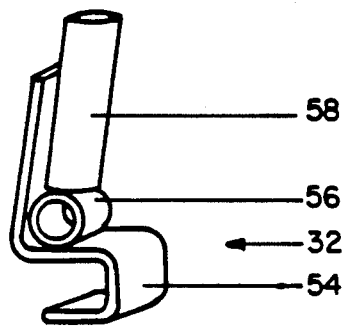
FIG. 4 shows the construction of a side-wall support bracket.
Figure 6:
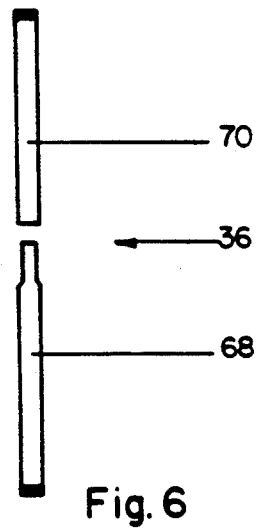
FIG. 6 shows the construction of a stabilizer member.
Figure 5:
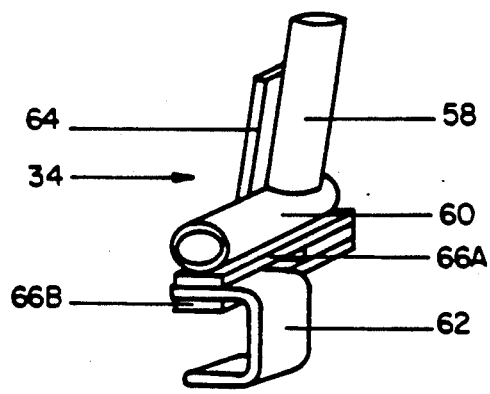
FIG. 5 shows the construction of a tailgate support bracket.
Figure 7:
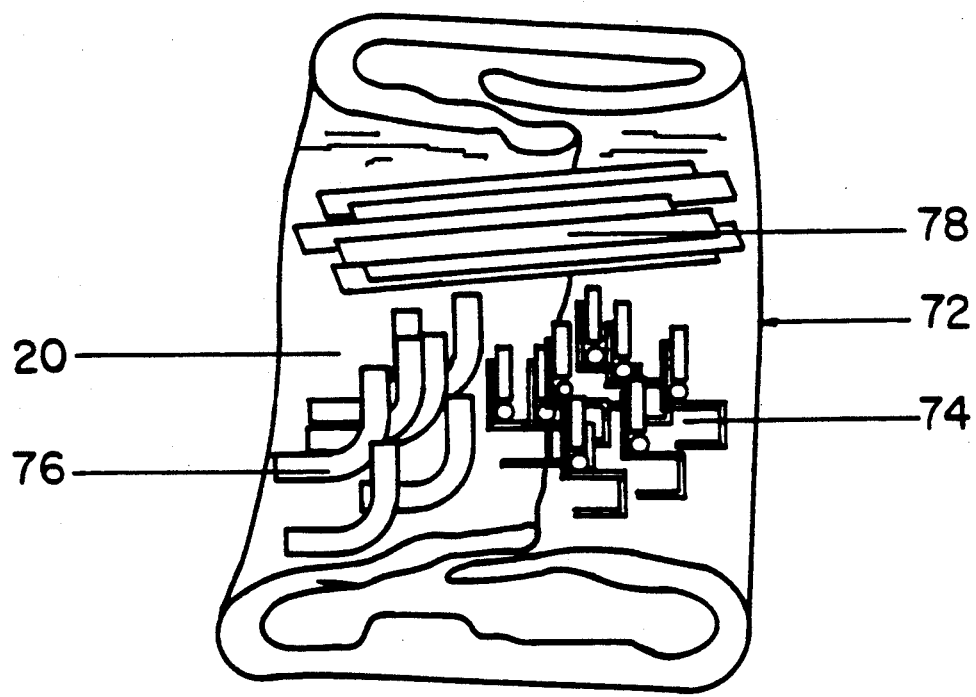
FIG. 7 shows the preferred storage method for the cover.
Figure 8:
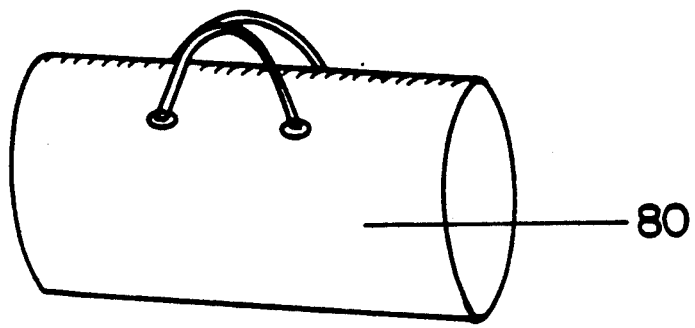
FIG. 8 shows a storage bag.

FIG. 4 shows the basic design of a side-wall support bracket (32). There are a total of eight side-wall support brackets (32). These brackets are used to secure the frame to the cargo bay side-wall ridge (82). The machine bent metal bracket (54) wraps around the side-wall ridge (82) and extends upward from the top of the side-wall ridge (82) at a slight angle toward the interior of the cargo bay. The securing tube (56) is attached to the machine bent metal bracket (54) by a weld or similar attachment. The receiving tube (58) is attached above the securing tube (56) by a weld or similar attachment. The entire side-wall support bracket can be dipped in liquid plastic or rubber for a coating to protect the side-wall ridge (82) from scratches. All eight of the side-wall support brackets (32) are exactly the same except for the first support bracket (closest to the cab) on each side. The first support bracket on each side has a plug (small piece of rod) welded or similarly attached to the end of the securing tube (56) closest to the cab. This is done to keep the stabilizer member from extending past the last support bracket.

Figure five shows a detail of one of the two tailgate support brackets (34). The tailgate support bracket (34) is attached to the side-wall ridge (82) by a machine bent "C" bracket (62). An upper and lower bracket extension (66A, 66B) is attached to the machine bent "C" bracket (62) by a weld or similar attachment. A receiving tube support bracket (64) is attached to the other end of the upper and lower bracket extensions (66A, 66B) by a weld or similar attachment. The receiving tube support bracket (64) extends upward from the top of the side-wall ridge (82) at a slight angle toward the interior of the cargo bay. An extended securing tube (60) is attached to the upper bracket extension (66A) by a weld or similar attachment. The end of the securing tube (60) (below the receiving tube (58)) is plugged to keep the stabilizer member from extending out past the end of the cargo bay. A receiving tube (58) is attached to the receiving tube support bracket (64) by a weld or similar attachment. The male end of the vertical support arm (44) will slide into the receiving tube (58).

Figure six shows the design of a stabilizer member (36). A stabilizer member (36) is simply made by connecting a tube with a female end (70) to a tube with a male end (68). Stabilizer members (36) slide into the securing tubes (56,60) to stabilize the support brackets (32,34). When all parts have been connected the main frame can be handled as one unit.

Figure seven shows how the invention can be rolled up for convenient storage. The assorted brackets (74), assorted tubes (78), and assorted elbows (76) can be conveniently rolled up inside the flexible cover (20) for storage. The entire invention can then be stored in a handy storage bag (80).

Figure eight shows the entire invention enclosed in a handy storage bag (80).

OPERATION—FIGS. 1, 2, 7, 8

The storage bag, containing the invention, is designed to conveniently be stored in the cargo bay or even the cab when not in use.

To use the cargo bay cover a person would first remove it from the storage bag (80). The support arms (38) would be assembled and slid through the fabric support arm sleeves (22). The stabilizer members (36) would be assembled and slid into the securing tubes of one tailgate support bracket and four side-wall support brackets (32). One of the two side-wall brackets, that has a plug in the securing tube, would be slid on last.

While still connected to the stabilizer member (36) each support bracket (32,34) would be attached to its corresponding support arm (38) to form the main frame. The flexible cover would then be secured to the support brackets (32,34) using the industrial snaps (24).

The cargo bay cover would then be lifted from one side and centered over the cargo bay. Pressure exerted against the side of the cargo bay cover, by pushing against the stabilizer member (36), would cause the brackets on the opposite side to slide into place around the side-wall ridge. The cover would then be lowered and the pressure released allowing the cover to snap into place.

When the cargo bay cover is not needed it can be broken down and stored in the storage bag (80) until it is needed again.

SUMMARY, RAMIFICATIONS, AND SCOPE

It is the purpose of this cargo bay cover to provide all of the advantages of the prior art with none of the disadvantages. While most of the prior art provides a suitable cover for the cargo bay, it is the purpose of this cargo bay cover to provide a lightweight, portable cover with no permanent attachments to the cargo bay.

Five support arms (38) are formed from two vertical support arms (44), two elbows (42), and an extension arm (40). The support arms (38) can be securely fastened to the support brackets (32,34) by sliding them into receiving tubes (58). The receiving tubes (58) are secured to the support brackets (32,34) that wrap around the side-wall ridge (82). Stabilizer members (36) are slid into the securing tubes (56) to connect the support brackets (32,34) and stabilize the cargo bay cover. The entire cargo bay cover can be dismantled and stored in a convenient storage bag (80).

The cargo bay cover can easily be installed or removed by one lay person in a reasonably short period of time. It is the purpose of this cargo bay cover to provide an inexpensive cover that can be easily installed, removed, and stored in a convenient storage bag (80).

While my above description contains many specificities, these should not be construed as limitations on the scope of the cargo bay cover, but rather as an exemplification of one preferred embodiment thereof. Many other variations are possible. For example, the above description will work for the most common pick-up truck bed (i.e. a double-sided hardbody with a cargo bay ridge). It can be easily foreseen that brackets will need to be designed to fit single-walled beds as well as step-side designs. Since these variations are endless, we have chosen not to include every possible bracket design, but simply the most common and most representative. A second example contemplates the method by which the individual components are attached. It is foreseeable that, with the use of hinges and similar attachments, the cargo bay cover could be collapsed without having to actually disconnect any parts. Accordingly, the scope of the cargo bay cover should be determined not by the embodiments illustrated, but by the appended claims and their legal equivalents. Thus the reader will see that the cargo bay cover provides a highly reliable, lightweight, and economical device that can be used by persons of almost any age.

I claim:

1. A removable cargo bay cover for pick-up trucks comprising:
   (a) a plurality of support arms of a generally inverted U-shape each having a pair of downardly extending leg portions;
   (b) a plurality of bracket supports each having a receiving tube for releasably receiving the lower end of respective of said downwardly extending leg portions and having an outwardly opening C-shaped member for engaging the top portion of a side wall of a truck bed;
   (c) a plurality of elongated stabilizer members each having end portions engagable with adjacent pairs of bracket supports;
   (d) means for releasably attaching a flexible protective cover to said support arms and said bracket supports.

2. The cover in claim 1 wherein said elongated support arms include a plurality of independent elongated members whereby said elongated support arms may be lengthened or shortened as desired.

3. The cover in claim 1, further including a means for storing said removable cargo bay cover in a flexible compact manner so as to allow for portability.

4. The cover in claim 1, further including a means for attaching said elongated support arms to said flexible cover having an underside so as to proportionally space said elongated support arms.

5. The cover of claim 1, further including a flap in the rearmost portion attached to the flexible cover by a zipper whereby allowing easy entry and exit to the cargo bay.

6. The cover in claim 1 wherein said downwardly extending leg portions are attached to said bracket supports at near right angles.

7. The cover in claim 1, further including elastic bands attached to said flexible cover and attached to the pick-up truck by a hook so as to keep said flexible cover from flapping when the pick-up truck is in operation.

8. The cover in claim 1 wherein no tools are required for assembly or installation.

9. The cover in claim 1 wherein said cover can be installed with one downwardly thrusting movement.

10. A removable cargo bay cover for trucks comprising:
    (a) a plurality of elongated support arms of a generally inverted U-shape each having a pair of downwardly extending leg portions, and
    (b) a plurality of elongated stabilizer members of substantially the same length, and
    (c) a plurality of support brackets each having a receiving tube for releasably receiving the lower end of respective of said downwardly extending leg portions and having a tube for releasably engaging portions of said elongated stabilizer members and having an outwardly opening C-shaped member for engaging the top portion of a side-wall of a truck bed, and
    (d) means for releasably attaching a flexible protective cover to said support arms and said bracket supports.

11. The cover in claim 10 wherein said elongated support arms include a plurality of independent elongated members whereby said elongated support arms may be lengthened or shortened as desired.

12. The cover in claim 10, further including a means for storing said removable cargo bay cover in a flexible compact manner so as to allow for portability.

13. The cover in claim 10, further including a means for attaching said elongated support arms to said flexible cover having an underside so as to proportionally space said elongated support arms.

14. The cover of claim 10, further including a flap in the rearmost portion attached to the flexible cover by a zipper whereby allowing easy entry and exit to the cargo bay.

15. The cover in claim 10 wherein said downwardly extending leg portions are attached to said support brackets at near right angles.

16. The cover in claim 10, further including elastic bands attached to said flexible cover and attached to the pick-up truck by a hook so as to keep said flexible cover from flapping when the pick-up truck is in operation.

17. The cover in claim 10 wherein no tools are required for assembly or installation.

18. The cover in claim 10 wherein said cover can be installed with one downwardly thrusting movement.

* * * * *